(12) United States Patent
Alferness et al.

(10) Patent No.: US 8,753,315 B2
(45) Date of Patent: Jun. 17, 2014

(54) MANUAL BASAL BOLUS DRUG DELIVERY DEVICE

(75) Inventors: Clifton A. Alferness, Port Orchard, WA (US); John M. Adams, Snohomish, WA (US)

(73) Assignee: Calibra Medical, Inc., Redwood City, CA (US)

( * ) Notice: Subject to any disclaimer, the term of this patent is extended or adjusted under 35 U.S.C. 154(b) by 212 days.

(21) Appl. No.: 13/360,485

(22) Filed: Jan. 27, 2012

(65) Prior Publication Data

US 2012/0215175 A1 Aug. 23, 2012

Related U.S. Application Data

(60) Provisional application No. 61/444,121, filed on Feb. 17, 2011.

(51) Int. Cl.
  *A61M 5/142* (2006.01)
  *A61M 5/145* (2006.01)
  *A61M 5/14* (2006.01)

(52) U.S. Cl.
  CPC ........... *A61M 5/1424* (2013.01); *A61M 5/1454* (2013.01); *A61M 2005/1405* (2013.01)
  USPC ............................. 604/131; 604/151; 604/246

(58) Field of Classification Search
  CPC .................... A61M 5/142; A61M 2005/1402; A61M 5/1424
  USPC ................................. 417/544; 604/182, 506
  See application file for complete search history.

(56) References Cited

U.S. PATENT DOCUMENTS

| 4,236,516 | A | * | 12/1980 | Nilson | 604/214 |
|---|---|---|---|---|---|
| 5,413,564 | A | * | 5/1995 | Silver et al. | 604/232 |
| 5,807,312 | A | * | 9/1998 | Dzwonkiewicz | 604/30 |
| 6,213,981 | B1 | * | 4/2001 | Hiejima et al. | 604/185 |
| 6,270,481 | B1 | * | 8/2001 | Mason et al. | 604/181 |
| 2003/0040722 | A1 | * | 2/2003 | Massengale et al. | 604/255 |
| 2006/0122562 | A1 | * | 6/2006 | Needle et al. | 604/185 |
| 2007/0299401 | A1 | * | 12/2007 | Alferness et al. | 604/152 |
| 2012/0209182 | A1 | * | 8/2012 | Gray | 604/131 |
| 2012/0209193 | A1 | * | 8/2012 | Gray | 604/151 |

\* cited by examiner

*Primary Examiner* — Nicholas Lucchesi
*Assistant Examiner* — Gerald Landry, II

(57) ABSTRACT

A fully manually powered infusion device provides both basal and bolus delivery of a liquid medicament to a patient. In some embodiments, the device includes a main reservoir that supplies the liquid medicament, an outlet port that delivers the liquid medicament to the patient, a basal dispenser that delivers a substantially constant flow of the liquid medicament to the outlet port, and a manually actuated bolus pump that delivers a bolus dose of the liquid medicament from the main reservoir to the outlet when actuated. The basal medicament supply delivers a volume of the liquid medicament from the main reservoir to the basal dispenser consonant with each actuation of the bolus pump.

13 Claims, 6 Drawing Sheets

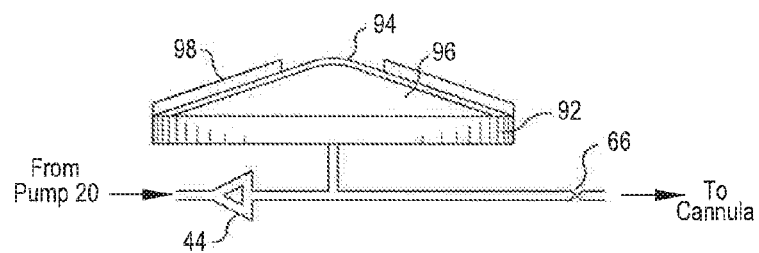
FIG. 4A
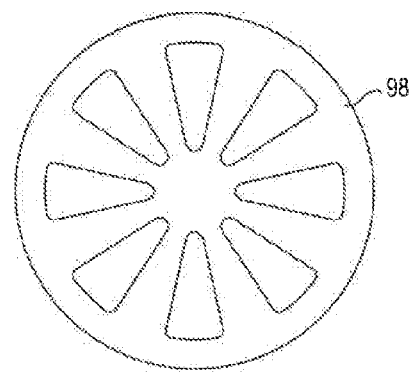
FIG. 5
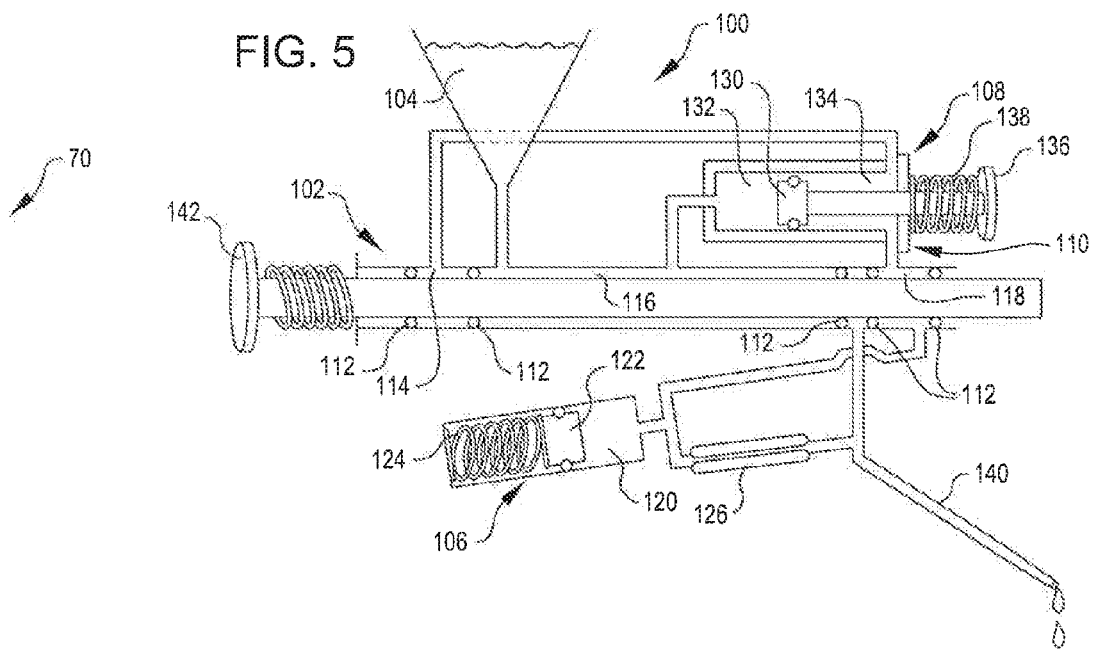

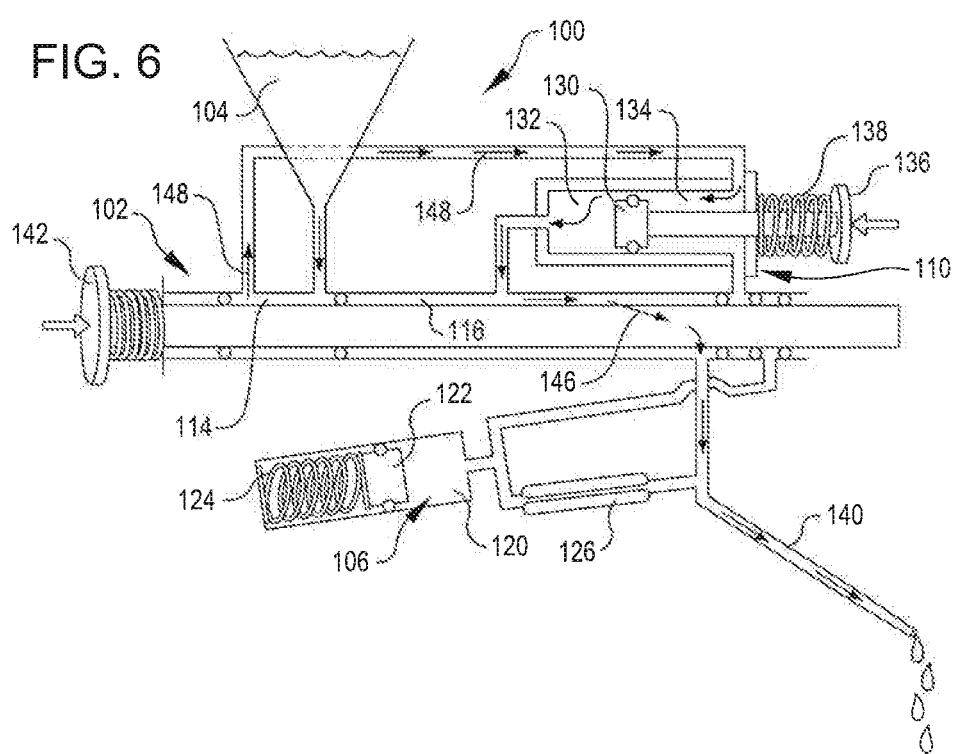
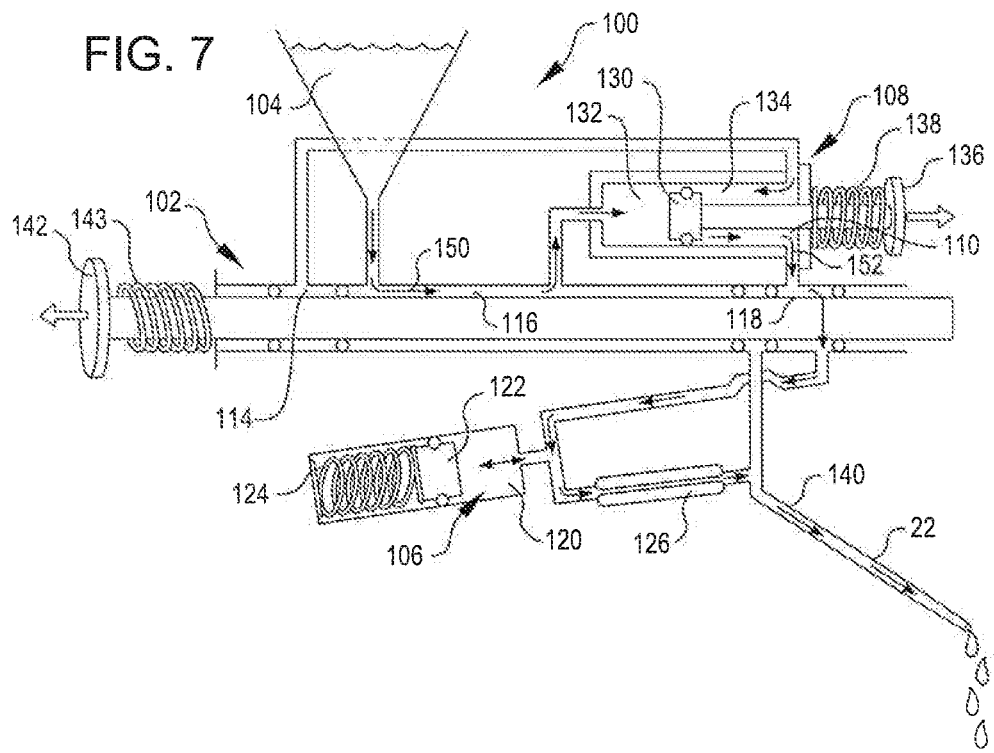

MANUAL BASAL BOLUS DRUG DELIVERY DEVICE

PRIORITY CLAIM

The present application claims the benefit of U.S. Provisional Patent Application Ser. No. 61/444,121, filed Feb. 17, 2011, which application is incorporated herein by reference in its entirety.

BACKGROUND OF THE INVENTION

The present invention relates to wearable infusion devices and more particularly to such devices that enable liquid medicaments to be conveniently and safely self-administered by a patient. The present invention is more particularly directed to such a wearable device that provides both bolus and basal medicament delivery and which is totally manually operable and powered. One liquid medicament that is often self-administered by a patient is insulin, and for ease of description, the administration of insulin is generally used herein for exemplary purposes although the invention should not be limited by that exemplary use.

Administration of insulin has traditionally been accomplished using a syringe. Recently, needle carrying pen-like devices have also been employed for this purpose. Both forms of insulin administration require the patients to stick themselves each time they inject insulin, often many times a day. Additionally, a new clean needle must be mounted on the device each time they are used, and disposed of after each use, creating the additional problem of having the "sharps" with them whenever the patient needs to administer insulin, and to safely dispose of them after each use. Thus, these traditional forms of insulin administration have been a rather pervasive intrusion in the lives and routines of the patients who have had to adopt and employ them.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such devices may involve fewer needle sticks, they are expensive to manufacture. They are also complex to operate and cumbersome and awkward to wear. Further, the cost of such devices can be many times the daily expense of using a traditional injection means such as a syringe or an insulin pen.

Devices of the type mentioned above also require a significant amount of training to control and thus use the devices. Great care in programming the devices is required because the pumps generally carry sufficient insulin to last a few days. Improper programming or general operation of the pumps can result in delivery of an excessive amount of insulin which can be very dangerous and even fatal.

Many patients are also reluctant to wear a pump device because they can be socially awkward. The devices are generally quite noticeable and can be as large as a pager. Adding to their awkwardness is their attachment to the outside of the patients clothes and the need for a catheter like tubing set running from the device to an infusion set located on the patient's body. Besides being obvious and perhaps embarrassing, wearing such a device can also be a serious impediment to many activities such as swimming, bathing, athletic activities, and many activities such as sun bathing where portions of the patient's body are necessarily uncovered.

In view of the above, a more cost effective and simple device has been proposed whereby an injection system is discreetly attached directly to the skin of the patient. One example of such a device is described in detail in U.S. application Ser. No. 12/147,283 filed Jun. 26, 2008 and titled DISPOSABLE INFUSION DEVICE WITH REDUNDANT VALVED SAFETY, which application is owned by the assignee of this application and incorporated herein by reference in its entirety. Such a device may be attached to the patient under the patient's clothing to deliver insulin into the patient by the manual pumping of small doses of insulin out the distal end of a temporarily indwelling cannula that is made a part of the pump device. The device may be made quite small and, when worn under the clothes, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For another description of devices of this type, reference may also be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

As may be seen from the above, wearable insulin delivery devices exist in either mechanical or electronic configurations. The mechanical devices do not contain batteries and the energy required is provided by the patient through squeezing buttons on the device attached to a small syringe. Currently available mechanical or manual devices provide bolus or meal time insulin nicely. However, the patient must inject one or more doses of long acting insulin daily to provide a basal supply of insulin. Therefore, a need exists to combine both basal and bolus insulin delivery in a single manual insulin pump in order to simplify dosing, ease pain and improve compliance. The present invention addresses these and other issues.

SUMMARY OF THE INVENTION

The present invention provides a fully manually powered infusion device that provides both basal and bolus delivery of a liquid medicament to a patient. The device includes a main reservoir that supplies the liquid medicament, an outlet port that delivers the liquid medicament to a patient, and a basal dispenser that delivers a substantially constant flow of the liquid medicament to the outlet port. The device further includes a manually actuated bolus pump that delivers a bolus dose of the liquid medicament from the main reservoir to the outlet when actuated and a basal medicament supply that delivers a volume of the liquid medicament from the main reservoir to the basal dispenser consonant with each actuation of the bolus pump.

The device may further include an overflow fluid path from the basal medicament supply to the main reservoir to permit the basal dispenser to be maintained in a full state.

The bolus pump may include a piston pump, the basal medicament supply may also include a piston pump, and the device may further include a common actuator that manually actuates the bolus piston pump and the basal medicament supply piston pump together.

The bolus piston pump and the basal medicament supply piston pump may each have a return stroke and the bolus piston pump and the basal medicament supply piston pump may be recharged with the liquid medicament from the main reservoir during the return strokes.

The bolus piston pump and the basal medicament supply piston pump may share a common piston and piston chamber. The basal medicament supply may be recharged as a bolus of the liquid medicament is delivered to the outlet, and the bolus pump may be recharged as the basal medicament supply delivers the volume of the liquid medicament to the basal dispenser.

The device may further include a shuttle valve that, when in a first position, establishes first concurrent flow paths for recharging the basal medicament supply and for delivering the bolus to the outlet and when in a second position, establishes second concurrent flow paths for recharging the bolus pump and for delivering the volume of the liquid medicament to the basal dispenser. The shuttle valve may establish an additional flow path from the basal dispenser to the reservoir when in the second position to provide overflow for maintaining the basal dispenser in a full state.

The basal dispenser may have a fill capacity and the basal medicament supply may fill the basal dispenser to its fill capacity with each actuation of the bolus pump. In this embodiment, the basal medicament supply may include a fluid path from the main reservoir to the basal dispenser. The fluid path may include a one way valve.

In another embodiment, the basal dispenser includes a reservoir and each actuation of the bolus pump causes liquid medicament from the main reservoir to be drawn into and fill the basal dispenser reservoir.

In some embodiments, the basal dispenser includes a supply chamber having a volume sufficient to enable the dispenser to deliver the substantially constant flow of the liquid medicament to the outlet port for an extended period of time.

The invention further provides a fully manually powered infusion device that provides both basal and bolus delivery of a liquid medicament to a patient. The device includes a main reservoir that supplies the liquid medicament, an outlet port that delivers the liquid medicament to the patient, a basal dispenser that delivers a substantially constant flow of the liquid medicament to the outlet port, and a manually actuated bolus pump that delivers a bolus dose of the liquid medicament from the main reservoir to the outlet when actuated wherein the basal dispenser delivers the substantially constant flow of the liquid medicament to the outlet port under energy stored as a direct result of and solely due to the manual actuation of the bolus pump.

BRIEF DESCRIPTION OF DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 4 shows an alternative embodiment of a basal medicament supply;

FIG. 4A is a plan view of the Belleville spring used in the embodiment of FIG. 4;

FIG. 5 is a schematic representation of a wearable bolus basal infusion device according to another embodiment of the present invention;

FIG. 6. illustrates the device of FIG. 5 with a shuttle valve therein in a first position establishing first concurrent flow paths for recharging the basal medicament supply and for delivering the bolus to the outlet;

FIG. 7. illustrates the device of FIG. 5 with the shuttle valve therein in a second position establishing second concurrent flow paths for recharging the bolus pump and for delivering the volume of the liquid medicament to the basal dispenser;

DETAILED DESCRIPTION OF THE INVENTION

Figure 1:
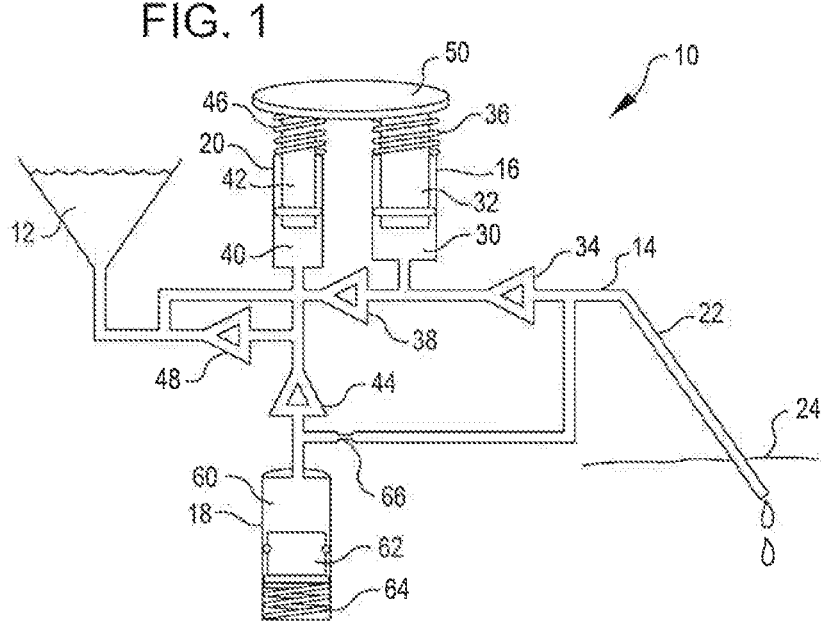
FIG. 1 is a schematic representation of a wearable bolus basal infusion device embodying the present invention.

Referring now to FIG. 1, it is a schematic representation of a wearable bolus basal infusion device 10 embodying the present invention. The device 10 generally includes a main reservoir 12, an outlet port 14, a bolus pump 16, a basal dispenser 18, and a basal medicament supply 20. The outlet port is fluidly coupled to a cannula 22 that extends to beneath the skin 24 of a patient to deliver medicament, such as insulin, to the patient. While the device 10 and other devices embodying the invention may be illustrated schematically herein, the device may be physically constructed by using the techniques and structure fully described in the aforementioned U.S. application Ser. No. 12/147,283 filed Jun. 26, 2008 and titled DISPOSABLE INFUSION DEVICE WITH REDUNDANT VALVED SAFETY, which application is owned by the assignee of this application and incorporated herein by reference in its entirety.

The bolus pump 16 is a piston pump including a chamber 30 and a piston 32 that forces medicament from the chamber 30, through a one-way valve 34, and to the outlet 14 to deliver a bolus of medicament to the patient. As the piston 32 is returned to its starting position by spring 36, the chamber 30 is recharged with medicament drawn from the reservoir 12 through a one-way valve 38.

The basal medicament supply 20 is also a piston pump. It includes a chamber 40 and a piston 42. The piston 42 forces medicament from the chamber 40 to the basal dispenser 18 through a one-way valve 44. As the piston 42 is returned to its starting position by spring 46, the chamber 40 is recharged with medicament drawn from the reservoir 12 through a one-way valve 48.

The basal medicament supply 20 and the bolus pump 16 share a common actuator 50. Hence, whenever a bolus of medicament is delivered to the patient by the depression of actuator 50, a volume of medicament is also transferred to the basal dispenser 18.

Figure 3:
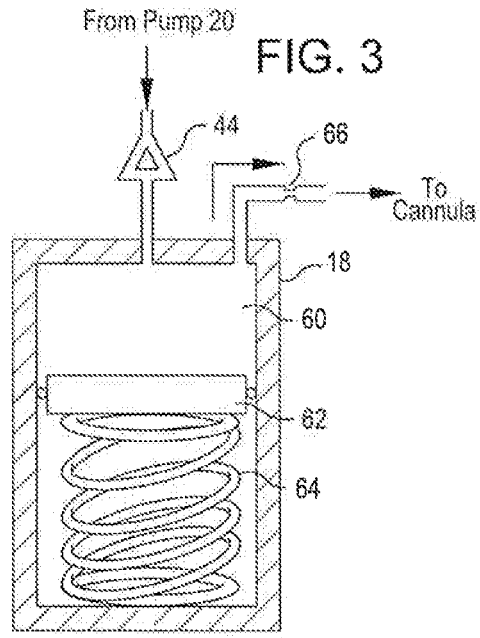
FIG. 3 is a more detailed view, in section, of the basal medicament supply of FIG. 1.

The basal dispenser 18, also shown in FIG. 3 in greater detail, is also a piston pump. It has a chamber 60 and a piston 62. The basal dispenser also includes a spring 64 that forces the piston 62 into the chamber 60 at a substantially constant rate to deliver basal therapy to the patient through a hydraulic restrictor 66.

The bolus dose piston pump 16 may be set, for example, to deliver 2 or 3 units of medicament. The basal medicament supply piston pump 20, which operates simultaneously with piston pump 16 when the patient pushes the actuator button 50, may contain a fixed, for example, smaller volume of medicament determined by the relative diameters of each of the chambers 30 and 40. The pressure generated by the tiny piston 42 can be very high and easily overcomes the spring tension of the spring 64 as the dispenser chamber 60 receives medicament. This basal insulin dose is stored in chamber 60 for delivery to the patient over a long period of time, i.e. several hours.

While the dose in piston pump 20 is stored in reservoir 60 during the compressive stroke of actuator 50, the bolus dose in piston pump 16 is directed to the outlet 14 and the cannula 22 through check valve 34 directly into the patient. The time period for delivering the basal dose is controlled by the pressure inside chamber 60 above ambient pressure and the hydraulic restrictor 66 between the basal medicament supply chamber 60 and the cannula 22. Hence, every time the patient delivers a bolus does of insulin, a fixed volume of insulin is recharged into the basal medicament supply chamber 60. Since patients have a normal ratio of basal to bolus need, the diameters or pistons 42 and 32 can be selected from a variety of available sizes to deliver the proper ratio of basal to bolus insulin. The diameter and length of the hydraulic restrictor 66 along with the compression force of spring 64 will determine the time course of the basal delivery. Such restrictors 66 are known in the art formed with micro laser drilling or porous metals.

The advantage of this embodiment of the invention is that a single reservoir 12 of insulin (usually fast acting) can be used to deliver both bolus and basal doses of insulin to the patient with the same manipulation of the actuator button of the device. No additional injections of slow acting insulin are needed while bolus dosing is being performed. Also, no complicated electronic basal flow device is needed. If a larger stroke volume is needed for the basal needs, the two pistons pumps 16 and 20 may be reversed and the larger one used for basal reservoir charging.

Figure 2:
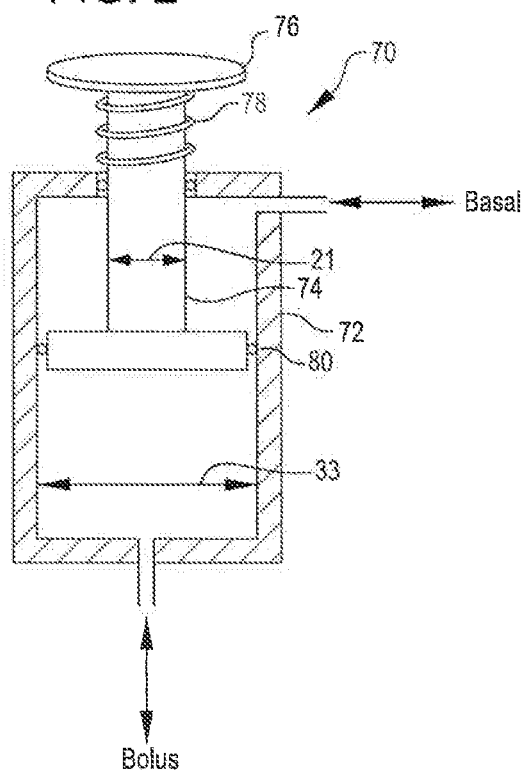
FIG. 2. is a detailed sectional view of a piston pump that may be employed to both deliver bolus doses and to provide the basal dispenser with medicament according to an embodiment of the invention.

FIG. 2 shows an alternative piston pump 70 that may be employed to both deliver bolus doses and to provide the basal dispenser with medicament according to another embodiment of the invention. The piston pump 70 displaces less volume in the device.

The piston pump 70 includes a piston cylinder 72 and a piston 74. A bolus of medicament is provided as the piston 74 is displaced into the cylinder. The stroke of the piston 74 times the area defined by diameter 33 determines the bolus dose per stroke of the piston 74 when the patient pushes actuator button 76. The basal dose per stroke is determined by the return stroke (the same as the push stroke) times the area defined by diameter 33 minus the area defined by diameter 21. The return stroke is performed by recovered energy in spring 78. When this alternative version is used, the return pressure in the basal chamber determined by spring 78 must be greater than the pressure needed to overcome the spring force of the spring 64 of the basal medicament dispenser chamber 60.

O-ring 80 provides a seal between the piston 74 and the inner wall of the piston cylinder 72. One or more O-rings may be used at any seal point for redundancy in this or in any other embodiment describe herein.

An alternative basal medicament supply is shown in FIGS. 4 and 4A. Here, the insulin is stored between a hard surface 92 and a flexible membrane 94 of a basal medicament dispenser reservoir 96. A Belleville spring 98, also seen in FIG. 4A, is used to provide a more constant pressure inside the reservoir 96. This provides a more even flow rate of the basal insulin dose.

Referring now to FIG. 5, it shows a wearable bolus basal infusion device according to another embodiment of the present invention. This embodiment 100 employs a shuttle valve 102 to establish the desired flow paths within the device. The device 100 generally includes the shuttle valve 102, a main reservoir 104, a basal dispenser 106, a manually actuated piston pump 108, and a basal medicament supply 110. The shuttle valve carries O-rings 112 that form a plurality of valves 114, 116, and 118.

The basal dispenser 106 is like the basal dispense 18 of FIG. 1. To that end it has a chamber 120 and a piston 122. The basal dispenser 106 also includes a spring 124 that forces the piston 122 into the chamber 120 at a substantially constant rate to deliver basal therapy to the patient through a hydraulic restrictor 126.

The piston pump 108 includes a piston 130. Chamber 132 is used to deliver bolus doses. Chamber 134, which forms a part of the basal medicament supply 110, provides the basal dispenser 106 with insulin during the return stroke of piston 130.

FIG. 6 illustrates the device of FIG. 5 with the shuttle valve 102 in a first position establishing first concurrent flow paths for recharging the basal medicament supply 110 and for delivering the bolus to the outlet 140. The shuttle valve 102 includes an actuator button 142 which has been depressed to a first position as shown in FIG. 6. With the actuator button 142 depressed, the piston actuator 136 may be depressed against the force of the spring 138. The depression of actuator 136 moves piston 130 into chamber 132 forcing the medicament therein along a path indicated by arrows 146 through valve 116 and to the outlet 140. This piston movement also causes medicament to be drawn from the reservoir 104 into chamber 134 of the basal medicament supply 110 along a path indicated by arrows 148 through valve 114.

FIG. 7 illustrates the device 100 of FIG. 5 with the shuttle valve 102 therein in a second position establishing second concurrent flow paths for recharging the bolus pump 108 and for delivering the volume of the liquid medicament from the basal medicament supply 110 to the basal dispenser 106. Here, the shuttle actuator 142 and valve 102 have been returned to a second or start position by spring 143. When the piston 130 thus returns to its start position under the force of spring 138, medicament will be drawn from the reservoir 104 along a path indicated by arrows 150, through valve 116 and into chamber 132 of the bolus piston pump 108. At the same time, medicament within chamber 134 of the basal medicament supply 110 is forced by piston 130 along a path indicated by arrows 152 through valve 118 and to the chamber 120 of the basal dispenser 106. Once this is completed, medicament is free to flow at a basal rate from the dispenser 106, through the hydraulic restrictor 126 and to the outlet 140.

As may be appreciated from the above, the device 100 is totally manually operated, actuated, and powered. Consonant with each basal delivery, a volume of medicament is also delivered to the basal dispenser 106 to support the basal therapy. The pressure in reservoir chamber 120 delivers a low dose basal rate to the patient through hydraulic resistance 126, the outlet 140, and the cannula 22. Thus bolus dosing recharges the basal reservoir and because of the fixed and relative volumes of chambers 132 and 134, provides the correct ratio of basal to bolus insulin.

At night time, when there is no meal boluses delivered, enough basal insulin will be needed for the duration of sleep and until the next bolus (usually a breakfast dose). This can be accommodated in different manners. For example, FIG. 8. is a schematic representation of a wearable bolus basal infusion device 160 according to another embodiment of the present invention that satisfies this need wherein a further shuttle valve 168 is provided to permit the basal medicament dispenser to be quickly filled with medicament. FIG. 9 illustrates the device 160 of FIG. 8 wherein the basal medicament dispenser is being filled. Since the device 160 is identical to the device 100 of FIGS. 5-7 (except as otherwise noted herein), the previous description of FIGS. 5-7 is repeated herein and like reference numerals for like elements are also repeated herein.

Figure 8:
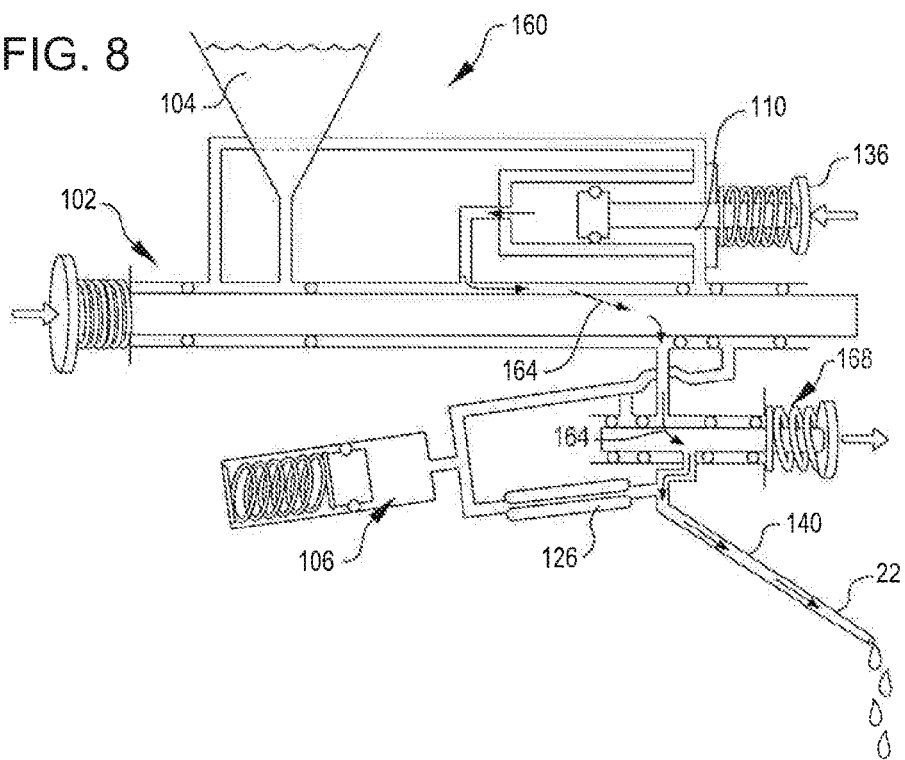
FIG. 8. is a schematic representation of a wearable bolus basal infusion device according to another embodiment of the present invention wherein a further valve is provided to permit the basal medicament dispenser to be quickly filled with medicament.
Figure 9:
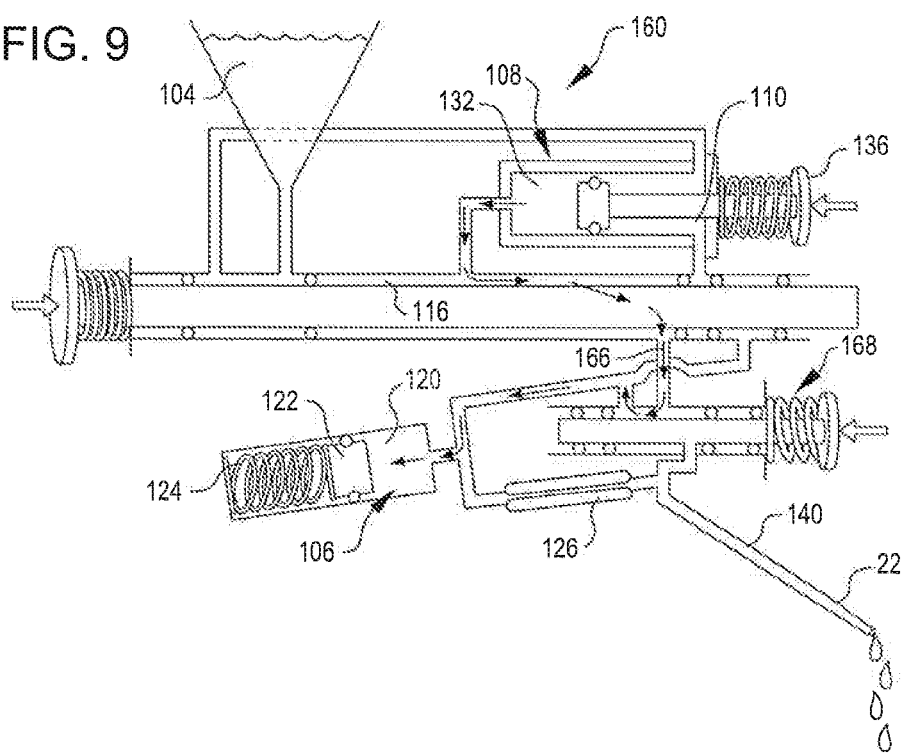
FIG. 9. illustrates the device of FIG. 8 wherein the basal medicament dispenser is being filled.

In the normal position shown in FIG. 8, the shuttle valve 168 directs a bolus of insulin to the outlet 140 and cannula 22 along a pathway indicated by arrows 164. In FIG. 9, the shuttle valve 168 has been depressed and held. Now when the actuator 136 is depressed, medicament within the chamber 132 is forced along a path indicated by arrows 166 from chamber 132, through valve 116 of shuttle valve 102, through the shuttle valve 168, and into chamber 120 of the basal dispenser 106. This allows for the loading of enough medicament to last an extended period of time, as for example eight to ten hours, or for a night time supply, in the basal dispenser chamber 120. This may be done prior to bedtime or for loading the basal dispenser chamber 120 when first attaching the device to the patient.

Figure 10:
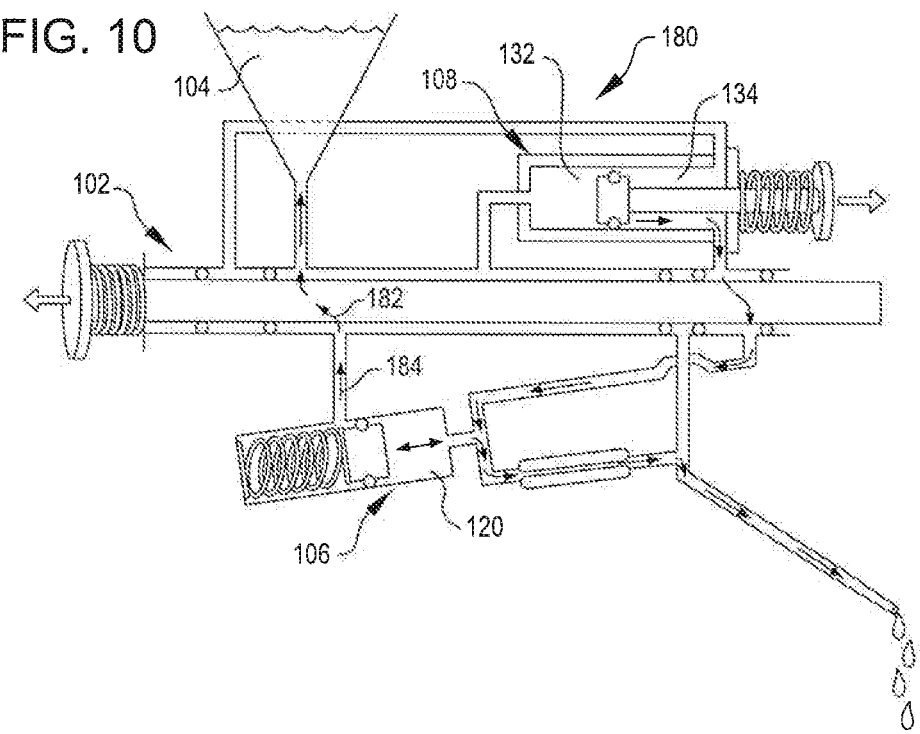
FIG. 10. illustrates a device similar to the device of FIGS. 5-7 wherein the basal medicament dispenser is being filled and wherein the device further includes over filling protection.

An alternative means of providing a sufficient supply of basal insulin is to keep the basal reservoir fully loaded with fewer button activations than is typically needed for bolus delivery. This is accomplished at each bolus dosing episode by having the basal loading dose much larger than the bolus dose. FIG. 10 illustrates a device 180 similar to the device 100 of FIGS. 5-7 wherein the basal medicament dispenser is being filled and wherein the device further includes over filling protection. Since the device 180 is identical to the device 100 of FIGS. 5-7, (except as otherwise noted herein) the previous description of FIGS. 5-7 is repeated herein and like reference numerals for like elements are also repeated herein.

FIG. 10 shows how a flow pathway, indicate by arrows 182, can be formed from the basal dispenser chamber 120 to the reservoir by a bypass conduit 184. The flow pathway 184 can provide a return path to the reservoir 104 whenever the chamber 120 of the basal dispenser 106 is full. This provides a facility to control the maximum volume of the insulin stored in the basal reservoir and assures a constant sufficient basal supply, all the time, merely by routine bolus dosing. In this mode the volume of piston chamber 134 may be increased to change the ratio of the relative volumes of chambers 132 and 134.

Figure 11:
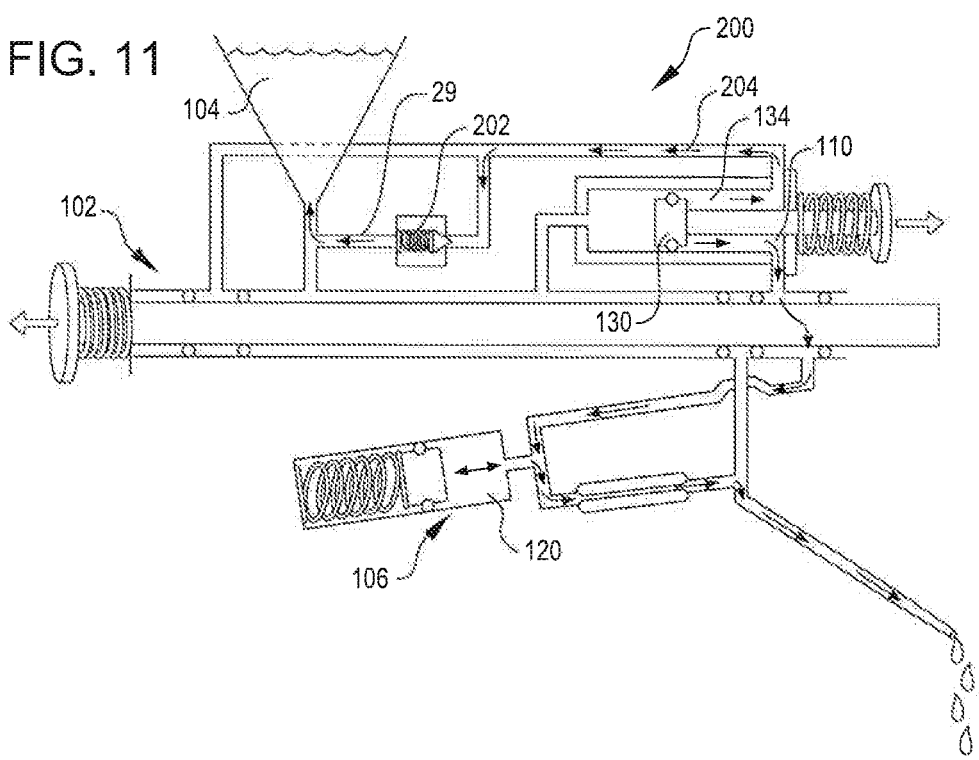
FIG. 11. illustrates another device similar to the device of FIGS. 5-7 with over filling protection.

FIG. 11 illustrates another device 200 similar to the device 100 of FIGS. 5-7 with over filling protection. Again, since the device 200 is identical to the device 100 of FIGS. 5-7 (except as otherwise noted herein) the previous description of FIGS. 5-7 is repeated herein and like reference numerals for like elements are also repeated herein. Here, unlike the device 100 of FIGS. 5-7, the device 200 includes a peak pressure pop off valve 202. The pressure in chamber 120, when it is filled and medicament is being forced from chamber 134 by piston 130 to fill chamber 120, will increase and open pressure relief valve 202. Excess medicament will return to the storage reservoir 104 through a flow pathway indicated by arrows 204 through the relief valve 202. This also will assure storage of sufficient medicament in the chamber 120 of the basal dispense 106 to last for an extended period of time for basal delivery such as, for example, eight to ten hours or overnight.

Figure 12:
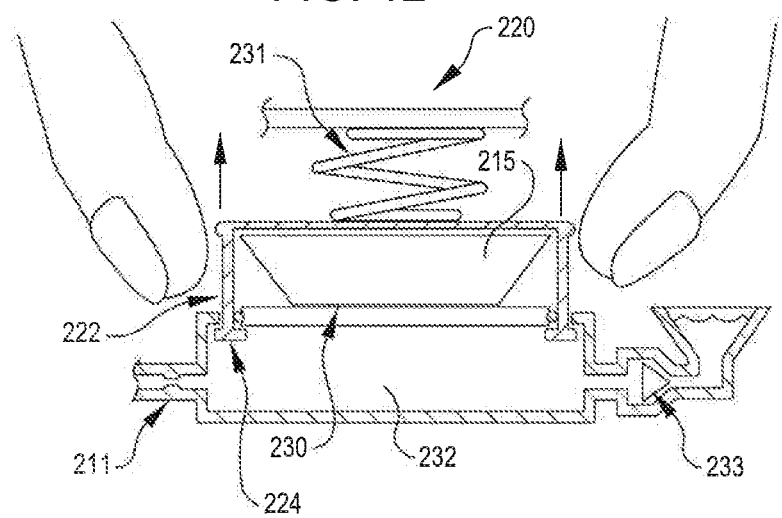
FIG. 12. is a side view, in section, of another device embodying the invention wherein the basal dispenser is fast filling.

FIG. 12 is a side view, in section, of another device 220 embodying the invention wherein the basal dispenser is fast filling. Rapid filling is accomplished by lifting chamber 222 either manually as shown or in conjunction with bolus activation. When this occurs, shoulder 224 lifts diaphragm 230 creating a negative pressure inside the basal reservoir 232. This causes check valve 233 to open rapidly filling the reservoir. When the chamber 222 is released, the force of spring 231 compresses the chamber 222 with a force in excess of that of spring 215. This then pressurizes the reservoir 232 to a pressure determined by the force of spring 215 and the surface area of the diaphragm 230 causing a substantially constant flow through resistance 211.

Figure 13:
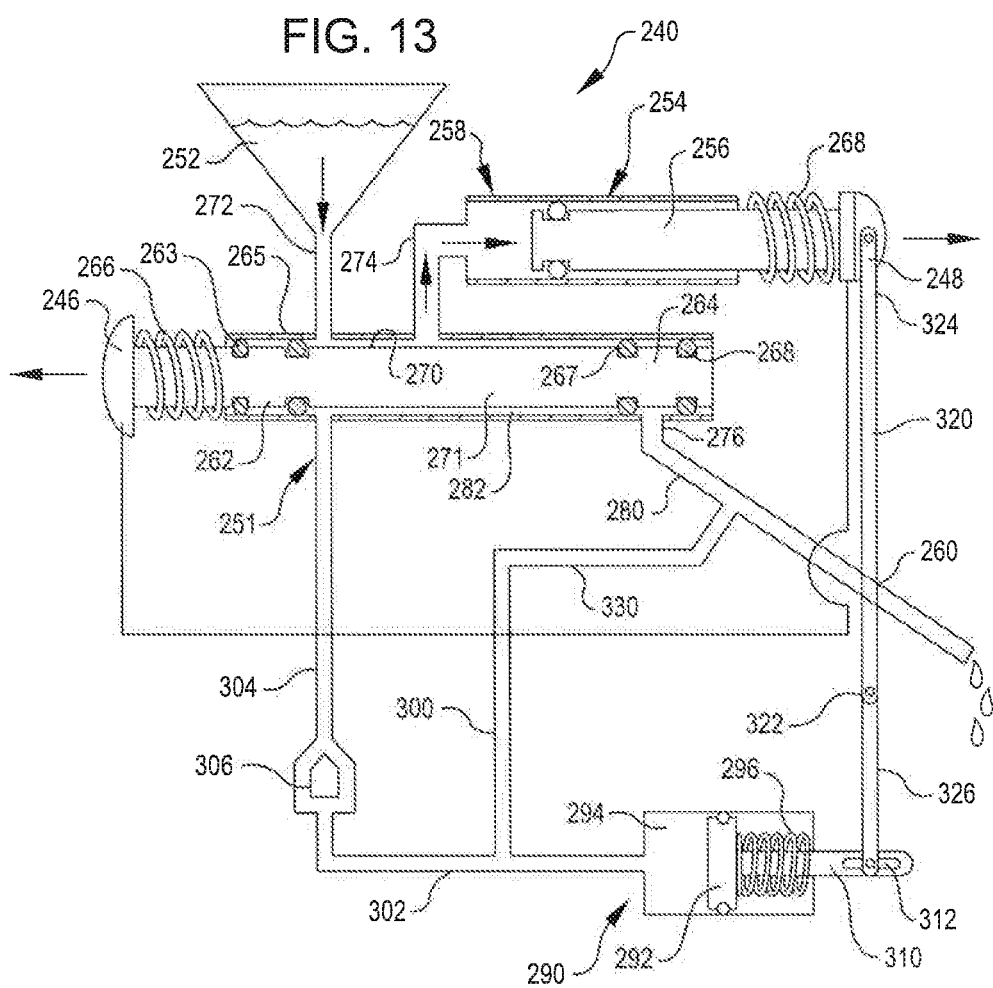
FIG. 13 is a schematic representation of another device embodying the invention wherein the basal dispenser is fast filling.

FIG. 13 is a schematic representation of another device 240 embodying the invention wherein the basal dispenser is fast filling. As may be seen in FIG. 13, the device 240 includes a reservoir 252, a bolus piston pump 254, a basal medicament dispenser 290, an outlet 280, and a cannula 260. The device further includes a shuttle valve 251 including piston 271 and forming a first valve 262 defined by O-rings 263 and 265 and a second valve 264 defined by O-rings 267 and 269. A fluid channel 282 defined by O-rings 265 and 267 is between the valves 262 and 264. Although O-rings are used herein to form seals, other types of valve construction may best employ forms of seals other than O-rings without departing from the invention. Fluid conduit 270 extends between the valves 262 and 264. A fluid conduit 272 provides a fluid connection between the reservoir 252 and the shuttle valve 251 and fluid conduit 274 provides a fluid connection between the shuttle valve 251 and the pump 254. A conduit 276 provides a fluid connection between the shuttle valve 261 and the device outlet 280. The outlet 280 is arranged to communicate with the cannula 260.

It may also be noted that the actuator buttons 246 and 248 are spring loaded by springs 266 and 268. The springs are provided for returning the actuator buttons to their start positions after a dosage is administered.

The pump 254 of the device 240 comprises a piston pump. The pump 254 includes a pump piston 256 and a pump chamber 258. The actuator control button 248 is directly coupled to and is an extension of the pump piston 256.

The basal dispenser 290 is a piston pump and includes a piston 292, a piston chamber 294, and a spring 296. The piston chamber 294 forms the reservoir for the basal dispenser 290. It is fluidly coupled to the outlet 280 by a conduit 300 and flow restrictor 330. It is also coupled to the shuttle valve 251 by conduits 302 and 304 and a one-way check valve 306.

The piston 292 has an extension 310 that includes a slot 312. A linkage 320 pivots about pivot point 322 and is connected to the actuator button 248 at one end 324 and to the extension 310 of the piston 292 by being captured in the slot 312 at the other end 326. However, the end 326 is free to slide within the slot 312.

In operation, with the shuttle valve 251 in the position shown in FIG. 13, the spring 268 is returning the actuator button 248 and the piston 256 to their starting positions. This causes medicament to be drawn from the reservoir 252 into chamber 258 to prepare the device 240 for the next bolus delivery.

During the next bolus delivery, the shuttle valve 251 is first depressed causing the channel 282 to communicate the piston chamber 258 with the conduit 276 and the outlet 280. It also causes the reservoir 252 to be isolated from the channel 282, conduit 276, and the outlet 280 and the reservoir to be in fluid communication with the conduit 304 through valve 262.

Now, depression of actuator button 248 causes the piston 256 to force the medicament in chamber 258 through conduit 274, channel 282, conduit 276 and to the outlet 280 for delivery to the cannula 260. The depression of the actuator button for the delivery of the bolus also causes linkage 320 to pivot about pivot point 322. This causes the end 326 of the linkage 320 to pull piston 292 against the spring 296. This in turn causes the chamber 294 to expand pulling medicament from the reservoir 252 and to the chamber 294 through the conduits 272, 304, and 302, the valve 262 of the shuttle valve 251, and the one-way valve 306. Hence, every time a bolus is delivered by the depression of actuator 248, the chamber 294 of the basal dispenser is filled to its capacity. Preferably, the capacity of the chamber 294 is sufficient to support ten continuous hours of basal delivery by the basal dispenser 290.

Basal delivery is achieved by the spring 296 moving piston 292 at a substantially constant rate. This causes medicament within the chamber 294 to flow at a substantially constant rate through conduit 300, through flow restrictor 330 and to the outlet 280 and cannula 260. The slot 312 within the piston extension 310 permits the spring 296 to push on the piston 292 in chamber 294.

Hence it may be seen from the foregoing that embodiments of the present invention provide an insulin delivery device that delivers fast acting insulin to provide both basal and bolus needs to a patient and is powered only by the mechanical action of the bolus pump actuators. Over a 24 hour time period, patients tend to use basal insulin in an approximately fixed ratio to the amount of bolus needed for mealtimes. As a result, a specific basal flow rate device can be selected from a variety of "sizes". In embodiments described herein, a substantially constant flow of insulin is delivered to provide the basal demand. In embodiments described herein, the devices are totally manual and require no external power supply. All pumping energy comes from the patient's fingers. During the day time or active time the devices have a piston pump that delivers the bolus amounts and simultaneously pumps a basal amount (in a predetermined ratio to the bolus) into a spring loaded reservoir. Pumping pressures generated by the small cylinders of some embodiments are very high, so the basal amount is easily loaded against the force of the basal dispenser spring loaded reservoir. The bolus medicament amount is delivered directly to the cannula but the basal medicament is stored for a metered delivery over time through that same cannula. The basal spring force delivers the basal amount through a flow restrictor (high hydraulic resistance) to the cannula. The resistance of the flow restrictor is chosen to deliver a substantially constant basal flow rate. Each bolus reloads the basal spring loaded pump. Special springs, known as Belleville springs, may be used for the basal reservoir to maintain a substantially constant force and resultant flow rate.

Because there are no bolus doses while the patient sleeps, in some embodiments, means are provided to load up the basal spring loaded pump (reservoir) with a volume sufficient to last throughout the night. In some embodiments, this is accomplished by holding down a third button in the device which directs the bolus piston to also pump into the basal reservoir. In this way a quick loading of the basal amount may be performed prior to bedtime or at any time. In other embodiments, a larger basal amount is delivered to the spring loaded reservoir with each bolus stroke such that every bolus dose refills the basal reservoir. With such embodiments, the device always has a sufficient overnight basal supply in the evening.

While particular embodiments of the present invention have been shown and described, modifications may be made, and it is therefore intended in the appended claims to cover all such changes and modifications which fall within the true spirit and scope of the invention as defined by those claims.

What is claimed:

1. A fully manually powered infusion device that provides both basal and bolus delivery of a liquid medicament to a patient, comprising:
   a main reservoir that supplies the liquid medicament;
   an outlet port that delivers the liquid medicament to a patient;
   a basal dispenser that delivers a substantially constant flow of the liquid medicament to the outlet port;
   a manually actuated bolus pump comprising a piston pump that delivers a bolus dose of the liquid medicament from the main reservoir to the outlet when actuated;
   a basal medicament supply comprising a piston pump that delivers a volume of the liquid medicament from the main reservoir to the basal dispenser consonant with each actuation of the bolus pump;
   wherein the bolus piston pump and the basal medicament supply piston pump each have a return stroke;
   a common actuator that manually actuates the bolus piston pump and the basal medicament supply piston pump together;
   wherein the bolus piston pump and the basal medicament supply piston pump are recharged with the liquid medicament from the main reservoir during the return strokes.

2. A fully manually powered infusion device that provides both basal and bolus delivery of a liquid medicament to a patient, comprising:
   a main reservoir that supplies the liquid medicament;
   an outlet port that delivers the liquid medicament to a patient;
   a basal dispenser that delivers a substantially constant flow of the liquid medicament to the outlet port;
   a manually actuated bolus pump comprising a piston pump that delivers a bolus dose of the liquid medicament from the main reservoir to the outlet when actuated;
   a basal medicament supply comprising a piston pump that delivers a volume of the liquid medicament from the main reservoir to the basal dispenser consonant with each actuation of the bolus pump, wherein the bolus piston pump and the basal medicament supply piston pump each have a return stroke;
   a common actuator that manually actuates the bolus piston pump and the basal medicament supply piston pump together;
   wherein the bolus piston pump and the basal medicament supply piston pump share a common piston and piston chamber, wherein the basal medicament supply is recharged as a bolus of the liquid medicament is delivered to the outlet, and wherein the bolus pump is recharged as the basal medicament supply delivers the volume of the liquid medicament to the basal dispenser.

3. The device of claim 1 or 2, further comprising an overflow liquid path from the basal medicament supply to the main reservoir to permit the basal dispenser to be maintained in a full state.

4. The device of claim 1 or 2, further comprising a shuttle valve that, when in a first position, establishes first concurrent flow paths for recharging the basal medicament supply and for delivering the bolus to the outlet and when in a second position, establishes second concurrent flow paths for recharging the bolus pump and for delivering the volume of the liquid medicament to the basal dispenser.

5. The device of claim 4, wherein the shuttle valve establishes an additional flow path from the basal dispenser to the reservoir when in the second position to provide overflow for maintaining the basal dispenser in a full state.

6. The device of claim 1 or 2, wherein the basal dispenser has a fill capacity and wherein the basal medicament supply fills the basal dispenser to its fill capacity with each actuation of the bolus pump.

7. The device of claim 6, wherein the basal medicament supply comprises a fluid path from the main reservoir to the basal dispenser.

8. The device of claim 7, wherein the fluid path includes a one way valve.

9. The device of claim 7, wherein the basal dispenser comprises a reservoir and wherein actuation of the bolus pump causes liquid medicament from the main reservoir to be drawn into and fill the basal dispenser reservoir.

10. The device of claim 1 or 2, wherein the basal dispenser includes a supply chamber having a volume sufficient to enable the dispenser to deliver the substantially constant flow of the liquid medicament to the outlet port for an extended period of time.

11. The device of claim 4 or 5, wherein the basal dispenser delivers the substantially constant flow of the liquid medicament to the outlet port under energy stored as a direct result of and solely due to the manual actuation of the bolus pump.

12. The device of claim 1, wherein the bolus piston pump and the basal medicament supply piston pump share a common piston and piston chamber, wherein the basal medicament supply is recharged as a bolus of the liquid medicament is delivered to the outlet, and wherein the bolus pump is recharged as the basal medicament supply delivers the volume of the liquid medicament to the basal dispenser.

13. The device of claim 1 or 2, wherein the volume of liquid medicament delivered to the basal dispenser is larger than the bolus dose of liquid medicament.

\* \* \* \* \*